United States Patent [19]
Stone

[11] Patent Number: 5,984,858
[45] Date of Patent: Nov. 16, 1999

[54] MENISCAL XENOGRAFTS

[75] Inventor: Kevin R. Stone, Mill Valley, Calif.

[73] Assignee: Crosscart, Inc., San Francisco, Calif.

[21] Appl. No.: 09/036,171

[22] Filed: Mar. 6, 1998

Related U.S. Application Data

[63] Continuation-in-part of application No. 08/483,256, Jun. 7, 1995, Pat. No. 5,865,849.

[51] Int. Cl.⁶ .................................................. A61F 2/38
[52] U.S. Cl. ............................................................. 600/20
[58] Field of Search .................................. 623/20, 18, 16, 623/11, 901

[56] References Cited

U.S. PATENT DOCUMENTS

| | | |
|---|---|---|
| 4,034,418 | 7/1977 | Jackson et al. . |
| 4,344,193 | 8/1982 | Kenny . |
| 4,400,833 | 8/1983 | Kurland . |
| 4,502,161 | 3/1985 | Wall . |
| 4,597,266 | 7/1986 | Entrekin . |
| 4,609,627 | 9/1986 | Goldstein . |
| 4,627,853 | 12/1986 | Campbell et al. . |
| 4,642,120 | 2/1987 | Nevo et al. . |
| 4,678,470 | 7/1987 | Nashef et al. . |
| 4,755,593 | 7/1988 | Lauren . |
| 4,776,853 | 10/1988 | Klement et al. . |
| 4,789,663 | 12/1988 | Wallace et al. . |
| 4,801,299 | 1/1989 | Brendel et al. . |
| 4,846,835 | 7/1989 | Grande . |
| 4,880,429 | 11/1989 | Stone . |
| 4,932,973 | 6/1990 | Gendler . |
| 5,007,934 | 4/1991 | Stone . |
| 5,067,962 | 11/1991 | Campbell et al. . |
| 5,071,741 | 12/1991 | Brockbank . |
| 5,078,744 | 1/1992 | Chvapil . |
| 5,092,894 | 3/1992 | Kenny . |
| 5,116,374 | 5/1992 | Stone . |
| 5,131,850 | 7/1992 | Brockbank . |
| 5,158,574 | 10/1992 | Stone . |
| 5,160,313 | 11/1992 | Carpenter et al. . |
| 5,171,273 | 12/1992 | Silver et al. . |
| 5,171,322 | 12/1992 | Kenny . |
| 5,171,660 | 12/1992 | Carpenter et al. . |
| 5,192,312 | 3/1993 | Orton . |
| 5,216,126 | 6/1993 | Cox et al. . |
| 5,303,311 | 4/1994 | Stone et al. . |
| 5,306,304 | 4/1994 | Gendler . |
| 5,358,525 | 10/1994 | Fox et al. . |
| 5,507,810 | 4/1996 | Prewett et al. . |
| 5,613,982 | 3/1997 | Goldstein . |
| 5,865,849 | 2/1999 | Stone ........................................ 623/18 |

FOREIGN PATENT DOCUMENTS

| | | | |
|---|---|---|---|
| 0128706 | 12/1984 | European Pat. Off. ................. | 623/18 |
| 0347496 | 12/1989 | European Pat. Off. ............... | 623/901 |
| WO 84/03036 | 8/1984 | WIPO . | |
| WO 95/26740 | 10/1995 | WIPO . | |
| WO 95/28412 | 10/1995 | WIPO . | |
| WO 95/33828 | 12/1995 | WIPO . | |

OTHER PUBLICATIONS

Rubak et al., *Acta Orthop. Scand*, 53:181–186 (1982).
Engkvist, Ove, *Scand. J. Plast. Reconstr. Surg.*, 13:361–369 (1982).
Collins et al., Xenotransplantation, Characterization of Porcine Endothelial Cell Determinants Recognized by Human Natural Antibodies, 1:36–46 (1994).
Satake et al., Xenotransplantation, Limited Specificity of Xenoantibodies In Diabetic Patients Transplanted With Fetal Porcine Islet Cell Clusters. Main Antibody Reactivity Against α–linked Galactose–Containing Epitopes, 1:89–101 (1994).
LaVecchio et al., Transplantation, Enzymatic Removal of Alpha–Galactosyl Epitopes From Porcine Endothelial Cells Diminishes The Cytotoxic Effect of Natural Antibodies, 60:841–847. (1995).
Stone et al., Arthroscopy: The Journal of Arthroscopic and Related Surgery, 9:234–237 (1993).
Cotterell et al., Transplantation, The Humoral Immune Response in Humans Following Cross–Perfusion of Porcine Organs, 60:861–868 (1995).
Galili, Immunology Today, 14:480–482 (1993).
Elves et al., An Investigation Into The Immunogenicity Of Various Components of Osteoarticular Grafts, *The British Journal of Experimental Pathology*, 55:344–351 (1974).
Rodrigo et al., *Clinical Orthopedics and Related Research*, 134:342–349 (1978).
Sengupta et al., *The Journal of Bone and Joint Surgery*, 56B:167–177 (1974).
Webber et al., *Journal of Orthopedic Research*, 3:36–42 (1985).

*Primary Examiner*—Jeffrey A. Smith
*Attorney, Agent, or Firm*—Lappin & Kusmer, LLP

[57] ABSTRACT

The invention provides an article of manufacture comprising a substantially non-immunogenic knee meniscal xenograft for implantation into humans. The invention further provides methods for preparing a knee meniscal xenograft by removing at least a portion of a meniscus from a non-human animal to provide a xenograft; washing the xenograft in saline and alcohol; and subjecting the xenograft to at least one treatment selected from the group consisting of exposure to ultraviolet radiation, immersion in alcohol, ozonation, and freeze/thaw cycling. In addition to or in lieu of the above treatments, the methods include a cellular disruption treatment and glycosidase digestion of carbohydrate moieties of the xenograft followed by treatment of carbohydrate moieties of the xenograft with capping molecules. The invention also provides articles of manufacture produced by one or more of the above-identified methods of the invention. The invention further provides a meniscal xenograft for implantation into a human including a portion of a meniscus from a non-human animal, wherein the portion includes extracellular matrix and substantially only dead cells. The matrix and dead cells have substantially no surface α-galactosyl moieties and have capping molecules linked to at least a portion of surface carbohydrate moieties. Each of the xenografts of the invention is substantially non-immunogenic and has substantially the same mechanical properties as the respective native meniscus.

22 Claims, 5 Drawing Sheets

MENISCAL XENOGRAFTS

RELATED APPLICATION

This application is a continuation-in-part of application U.S. Ser. No. 08/483,256, (now U.S. Pat. No. 5,865,849) filed Jun. 7, 1995.

FIELD OF THE INVENTION

The present invention relates to the field of treatment of injured human knee joints, and in particular, to replacement and repair of a damaged human knee joint meniscus using a substantially immunologically compatible meniscus from a non-human animal.

BACKGROUND OF THE INVENTION

The human knee is a complex joint containing spatially interrelated bones, ligaments, and cartilaginous structures which interact to create a variety of motions. Specifically, the femoral condyles articulate with the surface plateaus of the tibia, through the cartilaginous medial and lateral menisci, and all of these structures are held in place by various ligaments. By virtue of their cartilaginous nature, the medial and lateral menisci are structures comprised of cells called fibrochondrocytes and an extracellular matrix of collagen and elastic fibers as well as a variety of proteoglycans. Undamaged menisci provide shock absorption for the knee by ensuring proper force distribution, stabilization, and lubrication for the interacting bone surfaces within the knee joint, which are routinely exposed to repeated compression loading during normal activity. Much of the shock absorbing function of the medial and lateral menisci is derived from the elastic properties inherent to cartilage. When menisci are damaged through injury, disease, or inflammation, arthritic changes occur in the knee joint, with consequent loss of function.

Since joint cartilage in adults does not naturally regenerate to a significant degree once it is destroyed, damaged adult menisci have historically been treated by a variety of surgical interventions including removal and replacement with prosthetic devices. An artificial knee joint having a rigid plastic femoral member and a metal tibial member is disclosed in U.S. Pat. No. 4,034,418. A number of meniscus prostheses have been devised which employ resilient materials such as silicone rubber or natural rubber, as in U.S. Pat. No. 4,344,193 and U.S. Pat. No. 4,502,161. Additional deformable, flexible resilient materials for a meniscus prosthesis such as collagen, tendon, or fibrocartilage are disclosed in U.S. Pat. No. 5,092,894 and U.S. Pat. No. 5,171,322. A cartilage replacement apparatus constructed of polyethylene plastic filled with small ball bearings or gelatinous fluid is described in U.S. Pat. No. 5,358,525. However, the known artificial prostheses have been unsatisfactory for treatment of damaged menisci, since they are deficient in the elastic, and therefore in the shock-absorbing, properties characteristic of natural menisci. Moreover, the known artificial devices have not proven able to withstand the forces inherent to routine knee joint function.

The present inventor provided improved prosthetic menisci in several of his earlier patents (U.S. Pat. No. 4,880,429; U.S. Pat. No. 5,007,934; U.S. Pat. No. 5,116,374; and U.S. Pat. No. 5,158,574). These patents generally disclose prosthetic menisci formulated from dry, porous matrices of processed natural fibers such as reconstituted cross-linked collagen, which optionally include glycosaminoglycan molecules. Generally, the source of collagen for these prosthetic menisci has been animal Achilles tendons or skin. The reconstitution process removes non-collagenous materials such as glycoproteins, proteoglycans, lipids, native glycosaminoglycans, and the like, which may confer additional elastic properties to the original tissue.

Much of the structure and many of the properties of original tissues may be retained in transplants through use of heterograft or xenograft materials, that is, tissue from a different species than the graft recipient. For example, tendons or ligaments from cows or other animals are covered with a synthetic mesh and transplanted into a heterologous host in U.S. Pat. No. 4,400,833. Flat tissues such as pig pericardia are also disclosed as being suitable for heterologous transplantation in U.S. Pat. No. 4,400,833. Bovine peritoneum fabricated into a biomaterial suitable for prosthetic heart valves, vascular grafts, burn and other wound dressings is disclosed in U.S. Pat. No. 4,755,593. Bovine, ovine, or porcine blood vessel xenografts are disclosed in WO 84/03036. However, none of these disclosures describe the use of a xenograft for meniscus replacement.

Once implanted in an individual, a xenograft provokes immunogenic reactions such as chronic and hyperacute rejection of the xenograft. The term "chronic rejection", as used herein refers to an immunological reaction in an individual against a xenograft being implanted into the individual. Typically, chronic rejection is mediated by the interaction of IgG natural antibodies in the serum of the individual receiving the xenograft and carbohydrate moieties expressed on cells, and/or cellular and/or extracellular matrices of the xenograft. For example, transplantation of cartilage xenografts from nonprimate mammals (e.g., porcine or bovine origin) into humans is primarily prevented by the interaction between the IgG natural anti-Gal antibody present in the serum of humans with the carbohydrate structure Gal$\alpha$1-3Gal$\beta$1-4G1cNAc-R ($\alpha$-galactosyl or $\alpha$-gal epitope) expressed in the xenograft. K. R. Stone et al., *Porcine and bovine cartilage transplants in cynomolgus monkey: I. A model for chronic xenograft rejection*, 63 Transplantation 640–645 (1997); U. Galili et al., *Porcine and bovine cartilage transplants in cynomolgus monkey: II. Changes in anti-Gal response during chronic rejection*, 63 Transplantation 646–651 (1997). In chronic rejection, the immune system typically responds within one to two weeks of implantation of the xenograft.

In contrast with "chronic rejection", "hyper acute rejection" as used herein, refers to the immunological reaction in an individual against a xenograft being implanted into the individual, where the rejection is typically mediated by the interaction of IgM natural antibodies in the serum of the individual receiving the xenograft and carbohydrate moieties expressed on cells. This interaction activates the complement system causing lysis of the vascular bed and stoppage of blood flow in the receiving individual within minutes to two to three hours.

The term "extracellular matrix or matrices", as used herein, refer to collagen and elastic fibers as well a variety of proteoglycans, which are secreted by fibrochondrocytes during cartilage growth and which undergo slow turn-over.

Xenograft materials may be chemically treated to reduce immunogenicity prior to implantation into a recipient. For example, glutaraldehyde is used to cross-link or "tan" xenograft tissue in order to reduce its antigenicity, as described in detail in U.S. Pat. No. 4,755,593. Other agents such as aliphatic and aromatic diamine compounds may provide additional crosslinking through the side chain carboxyl groups of aspartic and glutamic acid residues of the collagen polypeptide. Glutaraldehyde and diamine tanning also increases the stability of the xenograft tissue.

Xenograft tissues may also be subjected to various physical treatments in preparation for implantation. For example, U.S. Pat. No. 4,755,593 discloses subjecting xenograft tissue to mechanical strain by stretching to produce a thinner and stiffer biomaterial for grafting. Tissue for allograft transplantation is commonly cryopreserved to optimize cell viability during storage, as disclosed, for example, in U.S. Pat. No. 5,071,741; U.S. Pat. No. 5,131,850; U.S. Pat. No. 5,160,313; and U.S. Pat. No. 5,171,660. U.S. Pat. No. 5,071,741 discloses that freezing tissues causes mechanical injuries to cells therein because of extracellular or intracellular ice crystal formation and osmotic dehydration.

SUMMARY OF THE INVENTION

The present invention provides a substantially non-immunogenic meniscal cartilage xenograft for implantation into a human in need of knee meniscus repair or replacement. The invention further provides methods for processing xenogeneic meniscal cartilage with reduced immunogenicity but with substantially native elasticity and load-bearing capabilities for xenografting into humans.

As described herein, the term "xenograft" is synonymous with the term "heterograft" and refers to a graft transferred from an animal of one species to one of another species. Stedman's Medical Dictionary, Williams & Wilkins, Baltimore, Md. (1995).

As described herein, the term "xenogeneic", as in xenogeneic graft, cartilage, etc., refers to a graft, cartilage, etc., transferred from an animal of one species to one of another species. Id.

The methods of the invention, include, alone or in combination, treatment with radiation, one or more cycles of freezing and thawing, treatment with a chemical cross-linking agent, treatment with alcohol or ozonation. In addition to or in lieu of these methods, the methods of the invention include a cellular disruption treatment and glycosidase digestion of carbohydrate moieties of the xenograft followed by treatment of carbohydrate moieties of the xenograft with capping molecules. After one or more of the above-described processing steps, the methods of the invention provide a xenograft having substantially the same mechanical properties as a native knee meniscus.

As described herein, the term "cellular disruption" as in, for example, cellular disruption treatment, refers to a treatment for killing cells.

As described herein, the term "capping molecule(s)", refers to molecule(s) which link with carbohydrate chains such that the xenograft is no longer recognized as foreign by the subject's immune system.

In one embodiment, the invention provides an article of manufacture comprising a substantially non-immunogenic knee meniscal xenograft for implantation into a human.

In another embodiment, the invention provides a method of preparing a meniscal xenograft for implantation into a human, which includes removing at least a portion of a medial or lateral meniscus from a knee joint of a non-human animal to provide a xenograft; washing the xenograft in water and alcohol; and subjecting the xenograft to at least one treatment selected from the group consisting of exposure to ultraviolet radiation, immersion in alcohol, ozonation, and freeze/thaw cycling, whereby the xenograft has substantially the same mechanical properties as the native meniscus.

As described herein, the term "portion", as in, for example, a portion of medial or lateral meniscus or a portion of surface carbohydrate moieties, refers to all or less than all of the respective medial or lateral meniscus or surface carbohydrate moieties.

In still another embodiment, the invention provides a method of preparing a meniscal xenograft for implantation into a human, which includes removing at least a portion of a medial or lateral meniscus from a knee joint of a non-human animal to provide a xenograft; washing the xenograft in water and alcohol; subjecting the xenograft to a cellular disruption treatment; digesting the xenograft with a glycosidase to remove substantially first surface carbohydrate moieties from the xenograft; and treating second surface carbohydrate moieties on the xenograft with capping molecules to cap at least a portion of the second surface carbohydrate moieties, whereby the xenograft is substantially non-immunogenic and has substantially the same mechanical properties as the native meniscus.

As described herein, the terms "to cap" or "capping", refer to linking a capping molecule such as a carbohydrate unit to the end of a carbohydrate chain, as in, for example, covalently linking a carbohydrate unit to surface carbohydrate moieties on the xenograft.

In further embodiments, the invention provides articles of manufacture including substantially non-immunogenic knee meniscal xenografts for implantation into humans produced by one or more of the above-identified methods of the invention.

In still a further embodiment, the invention provides a meniscal xenograft for implantation into a human which includes a portion of a medial or lateral meniscus from a knee joint of a non-human animal, wherein the portion includes an extracellular matrix and substantially only dead cells, the extracellular matrix and the dead cells having substantially no surface α-galactosyl moieties and having capping molecules linked to at least a portion of surface carbohydrate moieties. The portion of the medial or lateral meniscus is substantially non-immunogenic and has substantially the same mechanical properties as the native meniscus.

BRIEF DESCRIPTION OF THE DRAWINGS

The various features of the invention may be more fully understood from the following description when read together with the accompanying drawings.

DETAILED DESCRIPTION OF THE PREFERRED EMBODIMENTS

Figure 1:
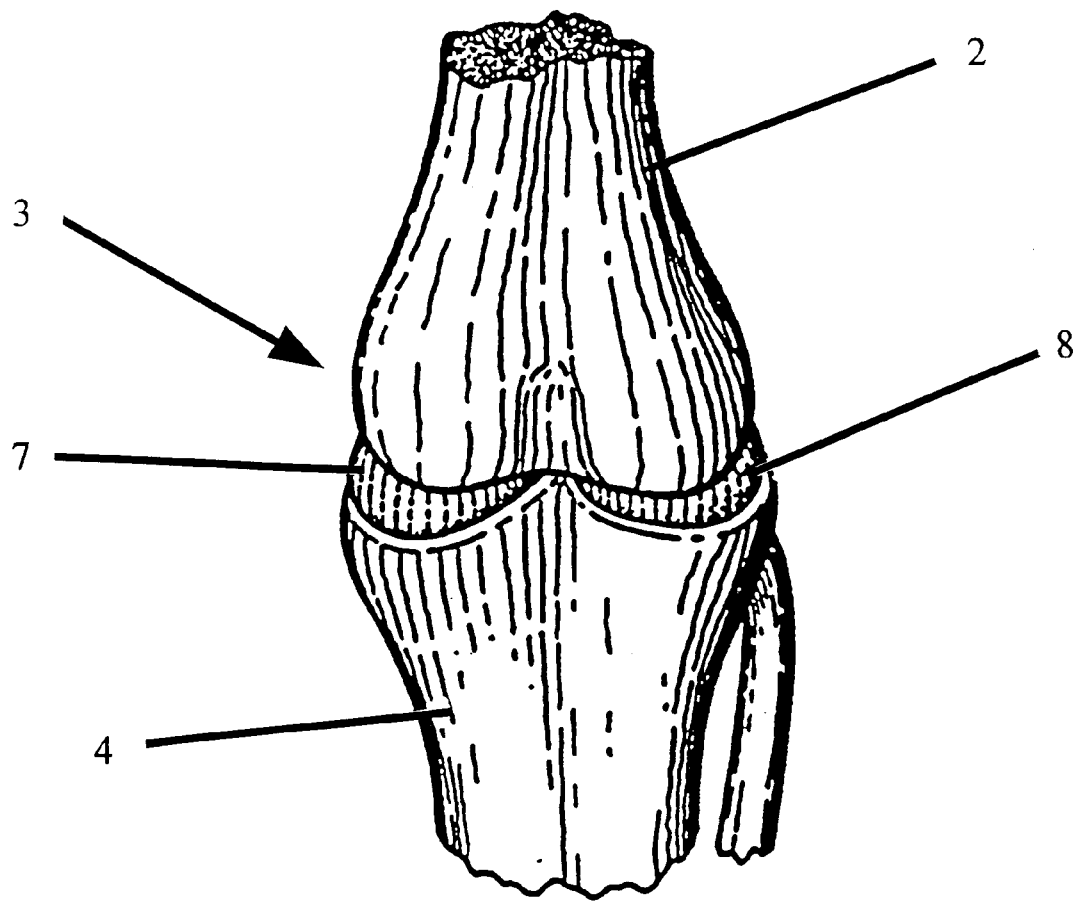
FIG. 1 shows a simplified diagrammatic representation of a human knee joint, with medial and lateral menisci in their native positions.

The present invention is directed against the chronic rejection of xenografts for implantation into humans. Accordingly, the meniscal xenograft produced in accordance with the method of the invention is substantially non-immunogenic, while generally maintaining the mechanical properties of a native meniscus.

While the meniscus may undergo some shrinkage during processing, a medial meniscus xenograft prepared in accordance with the invention will have the general appearance of a native medial meniscus, and a lateral meniscus xenograft of the invention will have the general appearance of a native lateral meniscus. The meniscal xenograft may also be cut into segments, each of which may be implanted into the knee of a recipient as set forth below.

The invention provides, in one embodiment, a method for preparing or processing a xenogeneic medial or lateral meniscus for engraftment into humans. The knee menisci may be harvested from any non-human animal to prepare the xenografts of the invention. Menisci from transgenic non-human animals or from genetically altered non-human animals may also be used as xenografts in accordance with the present invention. Preferably, bovine, ovine, or porcine knee joints serve as sources of the medial and lateral menisci used to prepare the xenografts. More preferably, immature pig, calf or lamb knee joints are the sources of the menisci, since the cartilage of younger animals may be inherently more elastic and engraftable than that of older animals. Most preferably, the age of the source animal is between six and eighteen months at time of slaughter.

In the first step of the method of the invention, an intact medial or lateral meniscus is removed from the knee of a non-human animal. The joint which serves as the source of the menisci should be collected from freshly killed animals and preferably immediately placed in a suitable sterile isotonic or other tissue preserving solution. Harvesting of the joints should occur as soon as possible after slaughter of the animal and preferably should be performed in the cold, i.e., in the approximate range of about 5° C. to about 20° C., to minimize enzymatic degradation of the meniscal tissue. The menisci are harvested from the joints in the cold, under strict sterile technique. The joint is opened by first transecting the patellar tendon. The horns of the menisci are dissected free of adhering tissue. A small amount of bone representing a substantially cylindrical plug of approximately five millimeters in diameter by five millimeters in depth may be left attached to the horns. The meniscal synovial junction is carefully identified and freed from the meniscus tissue itself, thereby forming the xenograft.

The xenograft is then washed in about ten volumes of sterile cold water to remove residual blood proteins and water soluble materials. The xenograft is then immersed in alcohol at room temperature for about five minutes, to sterilize the tissue and to remove non-collagenous materials.

A xenograft appears as a shiny "C"-shaped fibrous tissue, having generally a crescent-shaped principal surface on the top side (the "superior surface") and a generally crescent-shaped principal surface on the bottom side (the "inferior surface"), where the outer portions of the superior and inferior surfaces are joined by way of an outer lateral surface and the inner portions of the superior and inferior surfaces are joined by way of an inner lateral surface.

After alcohol immersion, the xenograft may be subjected to at least one of the following treatments: radiation treatment, treatment with alcohol, ozonation, one or more cycles of freezing and thawing, and/or treatment with a chemical cross-linking agent. When more than one of these treatments is applied to the xenograft, the treatments may occur in any order.

In one embodiment of the method of the invention, the xenograft may be treated by exposure to ultraviolet radiation for about fifteen minutes or gamma radiation in an amount of about 0.5 to 3 MegaRad.

In another embodiment, the xenograft may be treated by again being placed in an alcohol solution. Any alcohol solution may be used to perform this treatment. Preferably, the xenograft is placed in a 70% solution of isopropanol at room temperature.

In still another embodiment, the xenograft may be subjected to ozonation.

In a further embodiment of the method of the invention, the xenograft may be treated by freeze/thaw cycling. For example, the xenograft may be frozen using any method of freezing, so long as the xenograft is completely frozen, i.e., no interior warm spots remain which contain unfrozen tissue. Preferably, the xenograft is dipped into liquid nitrogen for about five minutes to perform this step of the method. More preferably, the xenograft is frozen slowly by placing it in a freezer. In the next step of the freeze/thaw cycling treatment, the xenograft is thawed by immersion in an isotonic saline bath at room temperature (about 25° C.) for about ten minutes. No external heat or radiation source is used, in order to minimize fiber degradation.

In yet a further embodiment, the xenograft may optionally be exposed to a chemical agent to tan or crosslink the proteins within the extracellular matrix, to further diminish or reduce the immunogenic determinants present in the xenograft. Any tanning or crosslinking agent may be used for this treatment, and more than one crosslinking step may be performed or more than one crosslinking agent may be used in order to ensure complete crosslinking and thus optimally reduce the immunogenicity of the xenograft. For example, aldehydes such as glutaraldehyde, formaldehyde, adipic dialdehyde, and the like, may be used to crosslink the collagen within the extracellular matrix of the xenograft in accordance with the method of the invention. Other suitable crosslinking agents include aliphatic and aromatic diamines, carbodiimides, diisocyanates, and the like. When glutaraldehyde is used as the crosslinking agent, for example, the xenograft may be placed in a buffered solution containing about 0.05 to about 5.0% glutaraldehyde and having a pH of about 7.4. Any suitable buffer may be used, such as phosphate buffered saline or trishydroxymethylaminomethane, and the like, so long as it is possible to maintain control over the pH of the solution for the duration of the crosslinking reaction, which may be from one to fourteen days, and preferably from three to five days. Alternatively, the xenograft can be exposed to a crosslinking agent in a vapor form, including, but not limited to, a vaporized aldehyde crosslinking agent, such as, for example, vaporized formaldehyde. The vaporized crosslinking agent can have a concentration and a pH and the xenograft can be exposed to the vaporized crosslinking agent for a period of time suitable to permit the crosslinking reaction to occur. For example, the xenograft can be exposed to vaporized crosslinking agent having a concentration of about 0.05 to about 5.0% and a pH of about 7.4, for a period of time which can be from one to fourteen days, and preferably from three to five days. Exposure to vaporized crosslinking agent can result in reduced residual chemicals in the xenograft from the crosslinking agent exposure. The crosslinking reaction should continue until the immunogenic determinants are substantially removed from the xenogeneic tissue, but the reaction should be terminated prior to significant alterations of the mechanical properties of the xenograft. When diamines are also used as crosslinking agents, the glutaraldehyde crosslinking should occur after the diamine crosslinking, so that any unreacted diamines are capped. After the crosslinking reactions have proceeded to completion as described above, the xenograft should be rinsed to remove residual chemicals, and 0.01–0.05 M glycine may be added to cap any unreacted aldehyde groups which remain.

In addition to or in lieu of the above treatments, the xenograft can be subjected to a cellular disruption treatment to kill the xenograft's fibrochondrocytes, which precedes or follows digestion of the xenograft with glycosidases to remove surface carbohydrate moieties from the xenograft. The glycosidase digestion in turn can be followed by linkage with capping molecules to cap surface N-acetyllactosamine ends of carbohydrate chains of the xenograft.

In an embodiment of this method of the invention, the xenograft is subjected to a cellular disruption treatment to kill the fibrochondrocytes of the meniscus cartilage prior to in vitro digestion of the xenograft with glycosidases. Typically after surface carbohydrate moieties have been removed from nucleated cells and the extracellular matrix, nucleated, i.e., living cells reexpress the surface carbohydrate moieties. Reexpression of antigenic moieties of a xenograft can provoke continued immunogenic rejection of the xenograft. In contrast, non-nucleated, i.e., dead cells, are unable to reexpress surface carbohydrate moieties. Removal of antigenic surface carbohydrate moieties from the non-nucleated cells and extracellular matrix of a xenograft substantially permanently eliminates antigenic surface carbohydrate moieties as a source of immunogenic rejection of the xenograft.

Accordingly, in the above-identified embodiment, the xenograft of the present invention is subjected to freeze/thaw cycling as discussed above to disrupt, i.e., to kill the fibrochondrocytes of the meniscus cartilage. Alternatively, the xenograft of the present invention is treated with gamma radiation having an amount of 0.2 MegaRad up to about 3 MegaRad. Such radiation kills the fibrochondrocytes and sterilizes the xenograft. Once killed, the fibrochondrocytes are no longer able to reexpress antigenic surface carbohydrate moieties such α-gal epitopes which are factors in the immunogenic rejection of the transplanted xenografts.

Either before or after the fibrochondrocytes are killed, the xenograft is subjected to in vitro digestion of the xenograft with glycosidases, and specifically galactosidases, such as α-galactosidase, to enzymatically eliminate antigenic surface carbohydrate moieties. In particular, α-gal epitopes are eliminated by enzymatic treatment with α-galactosidases, as shown in the following reaction:

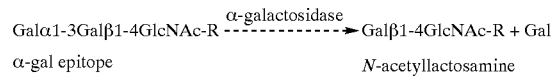

The N-acetyllactosamine residues are epitopes that are normally expressed on human and mammalian cells and thus are not immunogenic. The in vitro digestion of the xenograft with glycosidases is accomplished by various methods. For example, the xenograft can be soaked or incubated in a buffer solution containing glycosidase. In addition, the xenograft can be pierced to increase permeability, as further described below. Alternatively, a buffer solution containing the glycosidase can be forced under pressure into the xenograft via a pulsatile lavage process.

Elimination of the α-gal epitopes from the xenograft diminishes the immune response against the xenograft. The α-gal epitope is expressed in nonprimate mammals and in New World monkeys (monkeys of South America) as $1 \times 10^6$–$35 \times 10^6$ epitopes per cell, as well as on macromolecules such as proteoglycans of the extracellular matrix. U. Galili et al., *Man, apes, and Old World monkeys differ from other mammals in the expression of α-galactosyl epitopes on nucleated cells*, 263 J. Biol. Chem. 17755 (1988). This epitope is absent in Old World primates (monkeys of Asia and Africa and apes) and humans, however. Id. Anti-Gal is produced in humans and primates as a result of an immune response to α-gal epitope carbohydrate structures on gastrointestinal bacteria. U. Galili et al., *Interaction between human natural anti-α-galactosyl immunoglobulin G and bacteria of the human flora*, 56 Infect. Immun. 1730 (1988); R. M. Hamadeh et al., *Human natural anti-Gal IgG regulates alternative complement pathway activation on bacterial surfaces*, 89 J. Clin. Invest. 1223 (1992). Since nonprimate mammals produce α-gal epitopes, xenotransplantation of xenografts from these mammals into primates results in rejection because of primate anti-Gal binding to these epitopes on the xenograft. The binding results in the destruction of the xenograft by complement fixation and by antibody dependent cell cytotoxicity. U. Galili et al., *Interaction of the natural anti-Gal antibody with α-galactosyl epitopes: A major obstacle for xenotransplantation in humans*, 14 Immunology Today 480 (1993); M. Sandrin et al., *Anti-pig IgM antibodies in human serum react predominantly with Galα1-3Gal epitopes*, 90 Proc. Natl. Acad. Sci. USA 11391 (1993); H. Good et al., *Identification of carbohydrate structures which bind human anti-porcine antibodies: implications for discordant grafting in man.* 24 Transplant. Proc. 559 (1992); B. H. Collins et al., *Cardiac xenografts between primate species provide evidence for the importance of the α-galactosyl determinant in hyperacute rejection*, 154 J. Immunol. 5500 (1995). Furthermore, xenotransplantation results in major activation of the immune system to produce increased amounts of high affinity anti-Gal.

The cartilage xenografts of the present invention are particularly well suited to in vitro enzymatic elimination of the α-gal epitopes, however. In contrast to organs and other tissues, the cartilage extracellular matrix undergoes extremely slow turnover. Moreover, once the fibrochondrocytes are killed, these non-nucleated cells are prevented from reexpressing the α-gal epitopes, as discussed above. Accordingly, the substantial elimination of α-gal epitopes from cells and the extracellular matrix, and the prevention of reexpression of cellular α-gal epitopes can diminish the immune response against the xenograft associated with anti-Gal antibody binding with α-gal epitopes.

Following treatment with glycosidase, the remaining carbohydrate chains (e.g., glycosaminoglycans) of the xenograft are optionally treated with capping molecules to cap at least a portion of the remaining carbohydrate chains. Treatment with capping molecules is applicable to both glycosidase-treated and non-glycosidase-treated xenografts, however. For example, xenografts from knock out animals which may lack α-gal epitopes may be treated with capping molecules to cap carbohydrate moieties on the xenograft, thereby reducing the xenograft's immunogenicity. Examples of capping molecules used in the present invention include fucosyl and n-acetyl glucosamine.

Prior to treatment, the outer lateral surface of the xenograft may optionally be pierced to increase permeability to agents used to render the xenograft substantially non-immunogenic. A sterile surgical needle such as an 18 gauge needle may be used to perform this piercing step, or, alternatively a comb-like apparatus containing a plurality of needles may be used. The piercing may be performed with various patterns, and with various pierce-to-pierce spacings, in order to establish a desired access to the interior of the xenograft. Piercing may also be performed with a laser. In one form of the invention, one or more straight lines of punctures about three millimeters apart are established circumferentially in the outer lateral surface of the xenograft.

Prior to implantation, meniscal xenograft of the invention may be treated with limited digestion by proteolytic enzymes such as ficin or trypsin to increase tissue flexibility, or coated with anticalcification agents, antithrombotic coatings, antibiotics, growth factors, or other drugs which may enhance the incorporation of the xenograft into the recipient knee joint. The meniscal xenograft of the invention may be further sterilized using known methods, for example, with additional glutaraldehyde or formaldehyde treatment, ethylene oxide sterilization, propylene oxide sterilization, or the like. The xenograft may be stored frozen until required for use.

The meniscal xenograft of the invention, or a segment thereof, may be implanted into damaged human knee joints by those of skill in the art using known arthroscopic surgical techniques. Specific instruments for performing arthroscopic techniques are known to those of skill in the art, which ensure accurate and reproducible placement of meniscal implants. For meniscal cartilage replacement to succeed, the following goals are preferably accomplished:

1. The torn fragmented pieces of native meniscal cartilage must be removed.
2. The attachment sites for the meniscal horns must be anatomically placed.
3. The periphery of the meniscal implant must be attached securely enough to permit axial and rotational loads.
4. The surrounding capsule and ligaments of the knee joint must be neither excessively violated nor constrained by the fixation technique. The method of meniscal implantation described in detail below is derived from K. R. Stone, et al., *Arthroscopy: The Journal of Arthroscopic and Related Surgery* 9, 234–237 (1993); other methods of meniscal implantation may also be employed to use the xenogeneic meniscal xenografts of the present invention.

Figure 2:
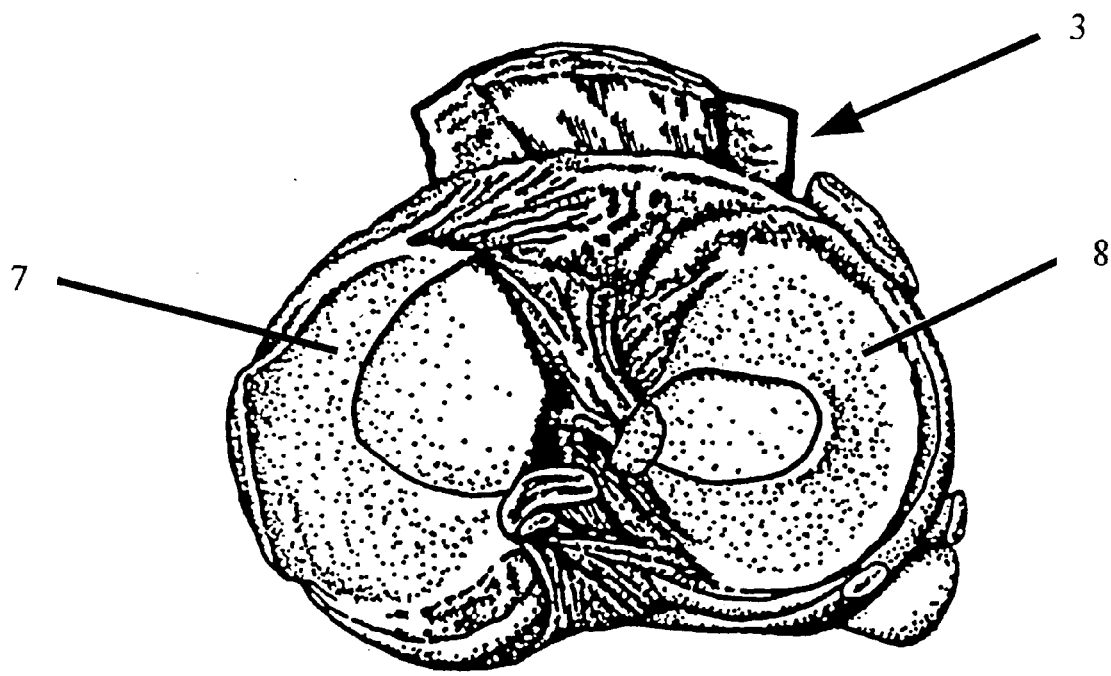
FIG. 2 is a diagrammatic representation of a cut-away view of a human knee joint, showing the medial and lateral menisci as they are positioned in vivo over the medial and lateral condyles of the tibia.

FIG. 1 shows a diagrammatic representation of the normal positioning of medical meniscus 7 and lateral meniscus 8 in the human knee joint 3 between the femur 2 and tibia 4. FIG. 2 shows the in vivo structure of medial meniscus 7 and lateral meniscus 8 in the knee joint 3.

Figure 3:
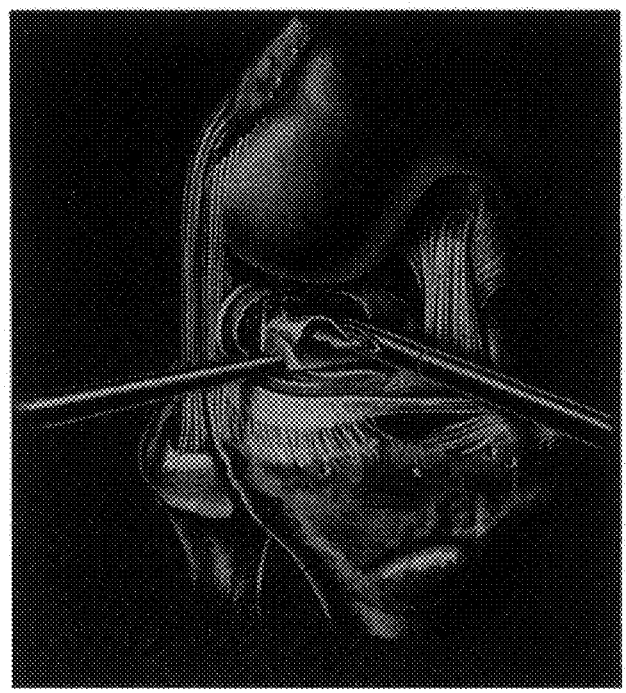
FIG. 3 is a diagrammatic representation of resection of a torn lateral meniscus of a human knee, and preparation of the knee for receipt of a meniscal implant.

Initially, complete diagnostic arthroscopy of the knee joint is accomplished using known methods. If anterior cruciate ligament surgery is to be performed simultaneously, the femoral and tibial tunnels for the cruciate reconstruction should be drilled first. The torn portion of the meniscal cartilage is evaluated. If meniscal repair cannot be accomplished due to severity of the tear or poor quality of the tissue, then preparation of the meniscal rim is undertaken by removing the torn portions of the cartilaginous tissue (FIG. 3). When the entire human meniscus is to be replaced by a xenogeneic meniscus xenograft of the invention, nearly all of the human meniscus is removed. Additionally, for replacement of the entire human meniscus with a xenogeneic meniscus xenograft of the invention, resection of the human meniscal horns and preparation of bony tunnels to accept bone plugs may be required. When only a portion of the human meniscus is to be replaced with a segment of the xenogeneic meniscus xenograft of the invention, only the damaged portions are removed, preserving the peripheral rim and horns for attachment of the xenogeneic meniscus xenograft segment. If absolutely no human meniscal rim is present, then partial replacement of the meniscus should not be performed. If the joint is excessively tight, a joint distractor may be applied or the medial collateral ligament may be partially released.

Figure 4:
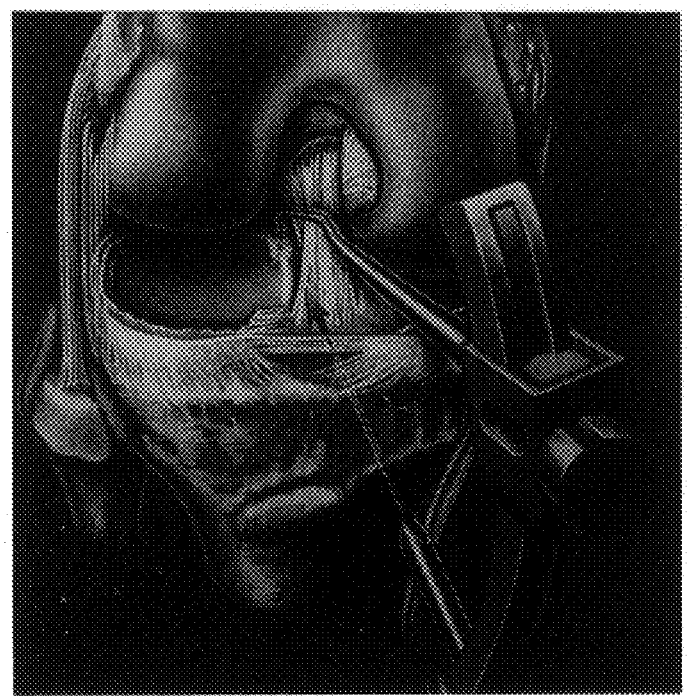
FIG. 4 is a diagrammatic representation the preferred drill guide placement for posterior lateral meniscal horn insertion into a human knee.
Figure 5:
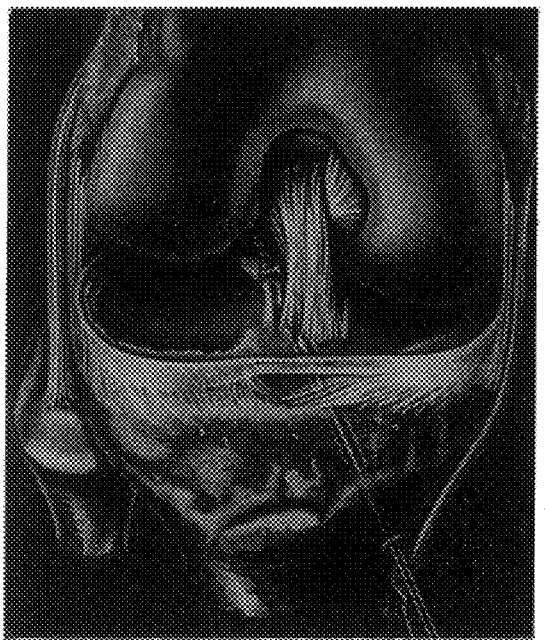
FIG. 5 is a diagrammatic representation of a cannulated drill overdrilling guide wire at the posterior lateral meniscal horn insertion into a human knee.

For medial or lateral meniscal replacement, the arthroscope is placed in the mid-lateral or anterior lateral portal and the tibial guide is placed through the anterior medial portal. The tip of the guide is brought first to the posterior horn of the meniscus. It should be noted that the posteromedial horn inserts on the posterior slope of the tibial eminence. A drill pin is then brought from the anterior medial side of the tibial tuberosity to the posterior horn insertion (FIG. 4). The pin placement can be confirmed by passing the arthroscope through the intercondylar notch and viewing the exit site of the pin. Extreme care must be undertaken to avoid penetration through the posterior capsule of the knee, endangering the neurovascular bundle. When the pin position is confirmed, the pin is then overdrilled with a 4.5-mm cannulated drill bit with the option of a drill stop to prevent posterior capsular penetration (FIG. 5). The bit is left in place and used as a tunnel for passage of a suture passer with a suture such as a #2 Ethibond™ suture available from Johnson & Johnson. The suture is passed up the bore of the drill bit, the drill bit removed, and the suture left in place.

Figure 6:
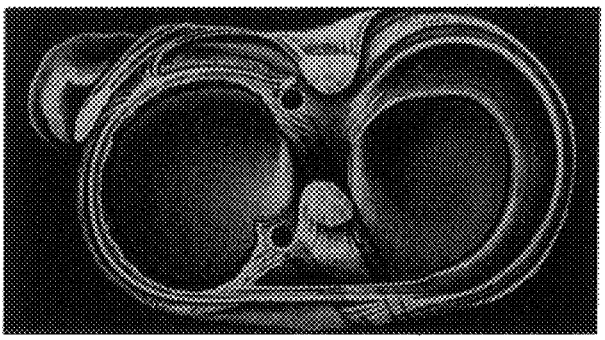
FIG. 6 is a diagrammatic representation of the appearance of a human knee with posterior and anterior drill holes for meniscal horn insertion.

The anterior medial meniscus insertion point in humans varies considerably, most often being found anterior to the medial tibial eminence. The anterior horn of the lateral meniscus inserts just posterior to the anterior cruciate ligament. An anterior drill hole is made by first identifying the insertion point of the anterior horn of the lateral meniscus, by placing the tip of the drill guide so that a relatively vertical hole will be made (FIG. 6). The drill pin is placed, then the cannulated drill bit is used to overdrill the drill pin placement to form the anterior drill hole. A suture passer is placed in the anterior drill hole. Alternatively, the anterior horn of the medial meniscus is affixed with a suture anchor directly to bone as opposed to a drill hole.

Before the suture is grasped from the anterior and posterior drill holes, the anterior portal is widened to approximately 2 cm. The suture grasper is then passed through the widened portal, and both the anterior and the posterior sutures brought out simultaneously. This technique prevents the sutures from becoming entangled in two different planes of the fat pad and capsular tissue.

Figure 7:
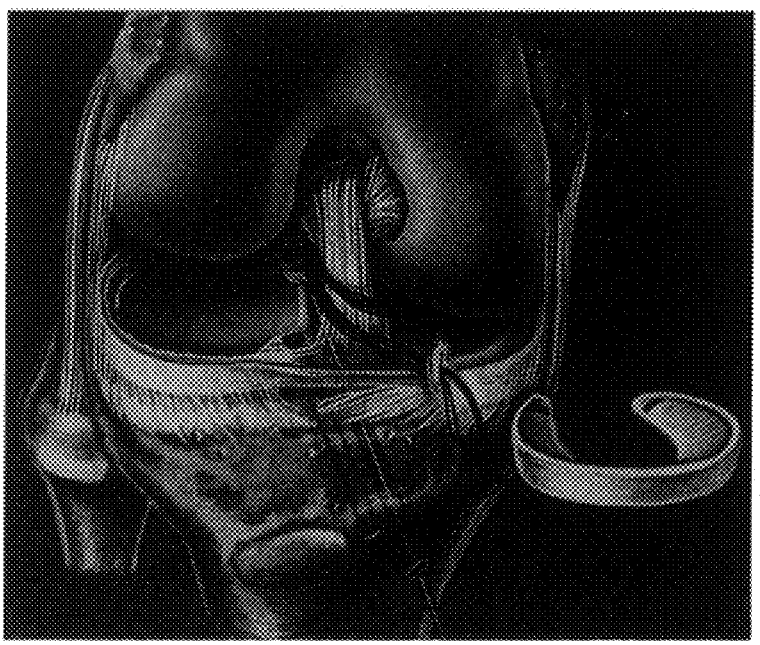
FIG. 7 is a diagrammatic representation of the preferred suture passer placement for pulling a meniscal implant into a human knee joint.
Figure 8:
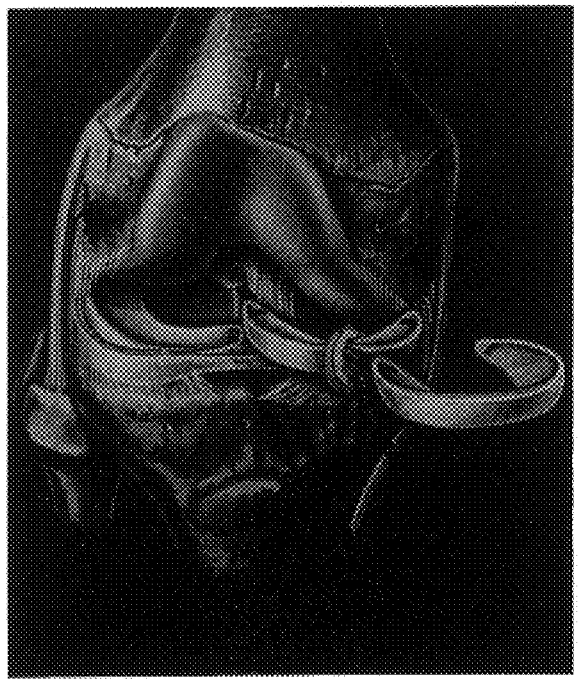
FIG. 8 is a diagrammatic representation of the appearance of a human knee containing a meniscal implant during the insertion stage.

The implant is now brought onto the field. Two horizontal mattress sutures, for example, #2-0 Ethibond™ sutures or the like, are placed through each horn of the xenogeneic meniscus xenograft with the free ends exiting the inferior surface (FIG. 7). The two posterior sutures are then drawn through the knee and out the posterior tibial tunnel (FIG. 8).

If viewing from a mid-lateral portal, the anterolateral portal can be used for probe insertion to push the implant medially into place through a 1-inch incision. No insertion cannula is required. The anterior sutures are then similarly passed. The horn sutures are then tied over the anterior tibial bony bridge.

Figure 9:
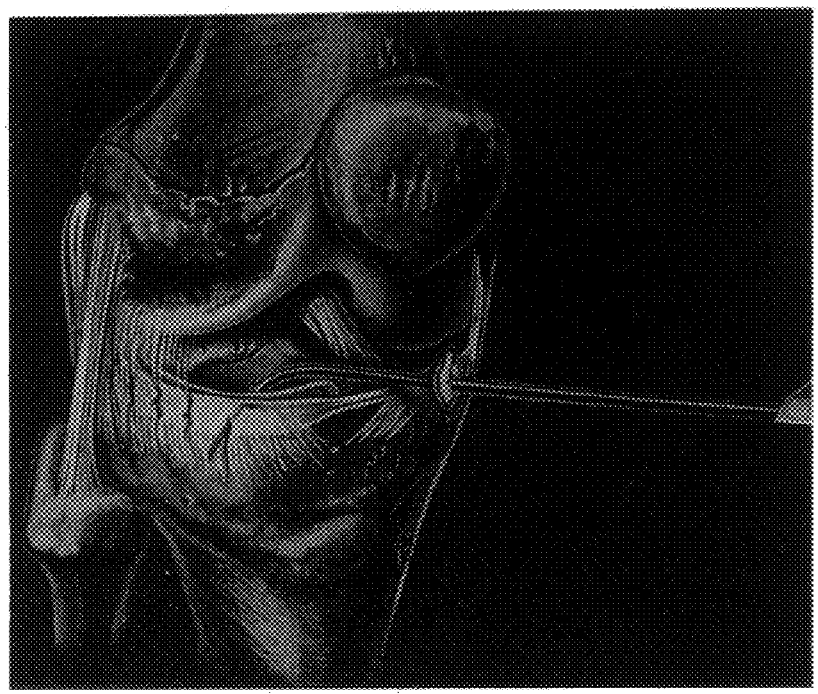
FIG. 9 is a diagrammatic representation of the appearance of a human knee containing a meniscal implant with zone-specific meniscal repair sutures in place for final tying of the meniscal repair sutures.

Next, zone specific meniscal repair cannulae are brought into place. For medial insertions, a posterior medial vertical incision is made one third of the distance from the back of the knee for protection of the saphenous nerve and for retrieval of the inside-out meniscal repair needles. A second vertical incision is usually required further anteriorly, next to the anterior medial arthroscopy portal, to capture the anterior exiting needles. Through these two incisions, the suture needles can be captured and the knots placed directly over the capsule (FIG. 9).

When using the meniscal repair needles, the posterior cannulae should be used first, with the sutures placed vertically and evenly spaced. The repair should proceed from posterior to anterior so that a buckle is not produced within the xenograft. Each knot is tied as it is placed to avoid the chance of suture tangling. The knots are spaced approximately 4 mm apart. The knee is cycled through several complete ranges of motion of ensure that the xenograft moves smoothly without impingement.

When performing a lateral meniscal replacement, the medial portal is suitable for xenograft insertion. This may require excision of the ligamentous mucosa and removal of a portion of the fat pad. The drill guide for the posterior horn of the lateral meniscus is inserted through the anteromedial portal. The posterior slope of the lateral tibial spine must be identified for accurate meniscal horn insertion. The anterior horn inserts on the anterior slope of the lateral tibial spine in approximation to the lateral aspect of the anterior cruciate ligament. The advantage of drilling these holes from the medial side is that the tunnel divergence will be greater, providing a larger bony bridge between the horn insertions. The remainder of the insertion technique remains the same, except that great care should be taken to protect the neurovascular bundle when suturing the posterior horn. Accessing posterolateral exposure is necessary to safeguard the common peroneal nerve and to expose the lateral capsule. If there is any doubt about the suture placement, open posterior horn suturing should be performed in the standard fashion. Alternatively, meniscus and/or stabilization devices such as arrows or staples can be used instead of sutures. Stabilization arrows manufactured by Bionix, Inc., Malvern, Pa., are non-limiting examples of such stabilization arrows. Other stabilization devices known to those of ordinary skill in the art can also be used.

Routine skin closure and dressings are applied. Thirty milliliters of 0.5% Marcaine (Astra) with epinephrine may be instilled if desired. A postoperative hinged knee brace is applied with the range of motion limited to 30° of extension and 90° of flexion.

Postoperatively the patient is permitted partial weight bearing in a hinged knee brace for six weeks. The brace is removed for sleeping and out-of-brace range-of-motion exercises. On day one after surgery, exercises are initiated for quad strengthening, including leg raises, quad sets, and well-leg bicycling. After six weeks, knee-bend exercises, two-leg bicycling, and water running exercises are initiated. When maximal strength gains are achieved, pivoting sports can be resumed, usually at four to six months after surgery.

This invention is further illustrated by the following Examples which should not be construed as limiting. The contents of all references and published patents and patent applications cited throughout the application are hereby incorporated by reference.

EXAMPLE 1

Assessment of Primate Response to Implanted Porcine Cartilage Treated With α-Galactosidase In this example, porcine cartilage implants are treated with α-galactosidase to eliminate α-galactosyl epitopes, the implants are transplanted into cynomolgus monkeys, and the primate response to the cartilage implants is assessed.

Porcine stifle joints are sterilely prepared and the meniscus cartilage and surrounding attached soft tissues surgically removed. The cartilage specimens are washed for at least five minutes with an alcohol, such as ethanol or isopropanol, to remove synovial fluid and lipid soluble contaminants.

The cartilage specimens are frozen at a temperature ranging from about −35° C. to about −90° C., and preferably at a temperature up to about −70° C., to disrupt, that, is to kill, the specimens' fibrochondrocytes.

The cartilage is cut into two portions. The first portion is immersed in a buffer solution containing α-galactosidase at a predetermined concentration. The specimens are allowed to incubate in the buffer solution for a predetermined time period at a predetermined temperature. The second cartilage portion is incubated under similar conditions as the first cartilage portion in a buffer solution in the absence of α-galactosidase and serves as the control.

At the end of the incubation, the cartilage is washed under conditions which allow the enzyme to diffuse out. Assays are performed to confirm the complete removal of the α-gal epitopes.

Each cartilage sample is implanted in the supra patellar pouch of six cynomolgus monkeys. With the animals under general inhalation anesthesia, an incision of about 1 cm is made directly into the supra patellar pouch at the superior medial border of the patella extending proximally. A piece of the porcine cartilage of about 0.5 cm to about 1 cm in length is placed into the pouch with a single 3-0 nylon stitch as a marking tag. The procedure is performed under sterile surgical technique, and the wounds are closed with 3-0 vicryl or a suitable equivalent known to those of ordinary skill in the art. The animals are permitted unrestricted cage activity and monitored for any sign of discomfort, swelling, infection, or rejection. Blood samples (e.g., 2 ml) are drawn periodically (e.g., every two weeks) for monitoring of antibodies.

The occurrence of an immune response against the xenograft is assessed by determining anti-Gal and non-anti-Gal anti-cartilage antibodies (i.e., antibodies binding to cartilage antigens other than the α-gal epitopes) in serum samples from the transplanted monkeys. At least two ml blood samples are drawn from the transplanted monkeys on the day of implant surgery and at periodic (e.g., two week) intervals post-transplantation. The blood samples are centrifuged and the serum samples are frozen and evaluated for the anti-Gal and other non-anti-Gal anti-cartilage antibody activity.

Anti-Gal activity is determined in the serum samples in ELISA with α-gal-BSA as solid phase antigen, according to methods known in the prior art, such as, for example, the methods described in Galili et al., *Porcine and bovine cartilage transplants in cynomolgus monkey: II. Changes in anti-Gal response during chronic rejection,* 63 Transplantation 645–651 (1997).

Assays are conducted to determine whether α-galactosidase treated xenografts induce the formation of anti-cartilage antibodies. For measuring anti-cartilage antibody activity, an ELISA assay is performed according to methods known in the prior art, such as, for example, the methods described in K. R. Stone et al., *Porcine and bovine cartilage transplants in cynomolgus monkey: I. A model for chronic xenograft rejection,* 63 Transplantation 640–645 (1997).

The cartilage is optionally explanted at one to two months post-transplantation, sectioned and stained for histological evaluation of inflammatory infiltrates. Post-transplantation changes in anti-Gal and other anti-cartilage antibody activities are correlated with the inflammatory histologic characteristics (i.e., granulocytes or mononuclear cell infiltrates) within the explanted cartilage, one to two months post-transplantation, using methods known in the art, as, for example, the methods described in K. R. Stone et al., *Porcine and bovine cartilage transplants in cynomolgus monkey: I. A model for chronic xenograft rejection,* 63 Transplantation 640–645 (1997).

Where the cartilage is explanted, the cartilage xenograft is aseptically harvested, using anesthetic procedure, surgical exposure of the joint, removal of the implant and closure of the soft tissue. At the time of the xenograft removal, joint fluid, if present in amounts sufficient to aspirate, is collected from the stifle joints for possible immunologic testing if the gross and histopathologic evaluation of the transplants indicate good performance of the transplanted cartilage. Subsequently, the animals are allowed to recover and are monitored closely until the incisions have healed and the gait is normal. The xenograft samples are collected, processed, and examined microscopically. A portion of the implant and surrounding tissue is frozen in an embedding medium for frozen tissue specimens in embedding molds for immunohistochemistry evaluation according to the methods known in the prior art. "TISSUE-TEK®" O.C.T. compound which includes 10.24% w/w polyvinyl alcohol, 4.26% w/w polyethylene glycol, and 86.60% w/w nonreactive ingredients, and is manufactured by Sakura FinTek, Torrence, Calif., is a non-limiting example of a possible embedding medium for use with the present invention. Other embedding mediums known to those of ordinary skill in the art may also be used. The remaining implant and surrounding tissue is collected in 10% neutral buffered formalin for histopathologic examination.

EXAMPLE 2

Assessment of Primate Response to Implanted Cartilage Treated With α-Galactosidase, Fucosyl and Fucosyltransferase In this example, porcine cartilage implants are treated with α-galactosidase to eliminate α-gal epitopes, as described in Example 1. The implants are further treated with fucosyl and fucosyl transferase to cap carbohydrate chains with fucosyl. Fucosyltransferase facilitates the transfer of fucosyl to the xenograft. The fucosyl links to and thus caps the carbohydrate chains. Capping with fucosyl interferes with the ability of the subject's immune system to recognize the xenograft as foreign. The implants are transplanted into cynomolgus monkeys, and the primate response to the cartilage implants is assessed.

Porcine cartilage stifle joints are prepared as described in Example 1 including the α-galactosidase treatment. Prior to implantation into the monkeys, however, the implants are further treated with a predetermined amount of fucosyl and fucosyltransferase, at specified concentrations for a predetermined time and at a predetermined temperature, to cap carbohydrate chains with fucosyl. For example, the sample is immersed in a buffer solution at predetermined concentrations of fucosyl and fucosyl transferase. The sample is incubated for a predetermined time period at a temperature.

Other molecules, such as n-acetyl glucosamine in combination with the corresponding glycosyltransferase, can also be used for capping the carbohydrate chains of the implants.

Subsequently, the samples are washed to remove the enzyme and implanted into the monkeys, and the occurrence of an immune response against the xenograft is assessed as described above in Example 1.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. A method of preparing a meniscal xenograft for implantation into a human, which comprises
   a. removing at least a portion of a medial or lateral meniscus from a knee joint of a non-human animal to provide a xenograft;
   b. washing the xenograft in water and alcohol;
   c. subjecting the xenograft to a cellular disruption treatment;
   d. digesting the xenograft with a glycosidase to remove substantially a plurality of first surface carbohydrate moieties from the xenograft; and
   e. treating a plurality of second surface carbohydrate moieties on the xenograft with a plurality of capping molecules to cap at least a portion of the second surface carbohydrate moieties, whereby the xenograft is substantially non-immunogenic and has substantially the same mechanical properties as the native meniscus.

2. The method of claim 1, wherein at least a portion of the capping molecules are a plurality of fucosyl molecules.

3. The method of claim 1, wherein at least a portion of the capping molecules are a plurality of n-acetyl glucosamine molecules.

4. The method of claim 1, wherein the glycosidase is a galactosidase.

5. The method of claim 4, wherein the galactosidase is an α-galactosidase.

6. The method of claim 1, wherein the cellular disruption treatment comprises freeze/thaw cycling.

7. The method of claim 1, wherein the cellular disruption treatment comprises exposure to gamma radiation.

8. The method of claim 1, wherein the removing step comprises removing the portion of the medial or lateral meniscus having a superior principal surface and an inferior principal surface, each of the principal surfaces having an outer portion being joined by an outer lateral surface, and each of the principal surfaces having an inner portion being joined by an inner lateral surface.

9. The method of claim 1 further comprising the step of following step c, exposing the xenograft to a crosslinking agent in a vapor form.

10. An article of manufacture comprising a substantially non-immunogenic knee meniscal xenograft for implantation in to a human, produced by a. removing at least a portion of a medial or lateral meniscus from a knee joint of a non-human animal to provide a xenograft;

b. washing the xenograft in water and alcohol;

c. subjecting the xenograft to a cellular disruption treatment;

d. digesting the xenograft with a glycosidase to remove substantially a plurality of first surface carbohydrate moieties from the xenograft; and e. treating a plurality of second surface carbohydrate moieties on the xenograft with a plurality of capping molecules to cap at least a portion of the second surface carbohydrate moieties, whereby the xenograft is substantially non-immunogenic and has substantially the same mechanical properties as the native meniscus.

11. The article of manufacture of claim 10, wherein at least a portion of the capping molecules are a plurality of fucosyl molecules.

12. The article of manufacture of claim 10, wherein at least a portion of the capping molecules are a plurality of n-acetyl glucosamine molecules.

13. The article of manufacture of claim 10, wherein the glycosidase is a galactosidase.

14. The article of manufacture of claim 13, wherein the galactosidase is an α-galactosidase.

15. The article of manufacture of claim 10, wherein the cellular disruption treatment comprises freeze/thaw cycling.

16. The article of manufacture of claim 10, wherein the cellular disruption treatment comprises exposure to gamma radiation.

17. The article of manufacture of claim 10, wherein the removing step comprises removing the portion of the medial or lateral meniscus having a superior principal surface and an inferior principal surface, each of the principal surfaces having an outer portion being joined by an outer lateral surface, and each of the principal surfaces having an inner portion being joined by an inner lateral surface.

18. The article of manufacture of claim 10 further comprising the step of following step c, exposing the xenograft to a crosslinking agent in a vapor form.

19. A meniscal xenograft for implantation into a human comprising a portion of a medial or lateral meniscus from a knee joint of a non-human animal, wherein the portion includes an extracellular matrix and a plurality of substantially only dead cells, the extracellular matrix and the dead cells having substantially no surface α-galactosyl moieties and having a plurality of capping molecules linked to at least a portion of a plurality of surface carbohydrate moieties on the xenograft, whereby the portion of the medial or lateral meniscus is substantially non-immunogenic and has substantially the same mechanical properties as the native meniscus.

20. The meniscal xenograft of claim 19, wherein at least a portion of the capping molecules are a plurality of fucosyl molecules.

21. The meniscal xenograft of claim 19, wherein at least a portion of the capping molecules are a plurality of n-acetyl glucosamine molecules.

22. The meniscal xenograft of claim 19, wherein the portion comprises a superior principal surface and an inferior principal surface, each of the principal surfaces having an outer portion being joined by an outer lateral surface, and each of the principal surfaces having an inner portion being joined by an inner lateral surface.

* * * * *